United States Patent
Midorikawa et al.

[11] Patent Number: 6,084,119
[45] Date of Patent: Jul. 4, 2000

[54] PROCESS FOR PRODUCING UNSATURATED NITRILE

[75] Inventors: Hideo Midorikawa; Ken Someya, both of Kurashiki, Japan

[73] Assignee: Asahi Kasei Kogyo Kabushiki Kaisha, Osaka, Japan

[21] Appl. No.: 09/142,605

[22] PCT Filed: Mar. 5, 1997

[86] PCT No.: PCT/JP97/00686

§ 371 Date: Sep. 8, 1998

§ 102(e) Date: Sep. 8, 1998

[87] PCT Pub. No.: WO97/33863

PCT Pub. Date: Sep. 18, 1997

[30] Foreign Application Priority Data

Mar. 12, 1996 [JP] Japan ................................. 8-054473

[51] Int. Cl.$^7$ ................................................. C07C 253/00
[52] U.S. Cl. .................................................. 558/324
[58] Field of Search ............................................. 558/324

[56] References Cited

U.S. PATENT DOCUMENTS

| | | |
|---|---|---|
| 3,882,159 | 5/1975 | Callahan et al. . |
| 4,052,332 | 10/1977 | D'Amore et al. . |
| 4,123,453 | 10/1978 | Grasselli et al. . |
| 4,139,552 | 2/1979 | Grasselli et al. . |
| 4,156,660 | 5/1979 | Grasselli et al. . |
| 4,162,234 | 7/1979 | Grasselli et al. . |
| 4,190,556 | 2/1980 | Grasselli et al. . |
| 4,192,776 | 3/1980 | Grasselli et al. . |
| 4,327,037 | 4/1982 | Grasselli et al. . |
| 4,377,534 | 3/1983 | Grasselli et al. . |
| 4,495,109 | 1/1985 | Grasselli et al. . |
| 4,503,001 | 3/1985 | Grasselli et al. . |
| 4,766,232 | 8/1988 | Grasselli et al. . |
| 4,767,878 | 8/1988 | Grasselli et al. . |
| 4,863,891 | 9/1989 | Grasselli et al. . |
| 5,177,048 | 1/1993 | Chen et al. . |
| 5,378,668 | 1/1995 | Beuke et al. . |

FOREIGN PATENT DOCUMENTS

| | | |
|---|---|---|
| 0 165 210 B1 | 10/1990 | European Pat. Off. . |
| 3311521 A1 | 1/1984 | Germany . |
| 51-6649 | 3/1976 | Japan . |
| 51-33888 | 9/1976 | Japan . |
| 55-49541 B2 | 12/1980 | Japan . |
| 56-52013 B2 | 12/1981 | Japan . |
| 59-76543 | 5/1984 | Japan . |
| 59-193136 | 11/1984 | Japan . |
| 59-50667 B2 | 12/1984 | Japan . |
| 60-36812 B2 | 8/1985 | Japan . |
| 2-56938 B2 | 12/1990 | Japan . |
| 4-227072 | 8/1992 | Japan . |
| 5-33100 B2 | 5/1993 | Japan . |

*Primary Examiner*—Johann Richter
*Assistant Examiner*—Joseph Murray
*Attorney, Agent, or Firm*—Pennie & Edmonds LLP

[57] ABSTRACT

A process for producing acrylonitrile or methacrylonitrile, wherein a molybdenum compound, which is convertible to molybdenum oxide and not supported on a carrier is added to a fluidized bed reactor as an activator, in such a way that the ratio y of molybdenum atoms in the oxide catalyst represented by the formula:

$$Mo_y Bi_p Fe_q A_a B_b C_c D_d E_e O_f$$

will be maintained in the range of 1.02x to 1.12x (x=1.5p+q+a+c+1.5d+1.5e) during an ammoxydation reaction.

6 Claims, No Drawings

PROCESS FOR PRODUCING UNSATURATED NITRILE

TECHNICAL FIELD

The present invention relates to a process for producing acrylonitrile or methacrylonitrile by carrying out a fluidized bed ammoxydation reaction using a multi-component oxide catalyst containing molybdenum, bismuth and iron, wherein a molybdenum compound is added as an activator to the fluidized bed reactor.

BACKGROUND ART

The process for producing acrylonitrile or methacrylonitrile by contacting propylene, isobutene or tertiary butanol with a catalyst in a vapor phase in the presence of ammonia and molecular oxygen has been widely known as ammoxydation reaction of olefins and industrially practiced. Many multi-component oxide catalysts containing molybdenum, bismuth and iron, which are usable for this reaction, have been disclosed in JP-B-51-6649, JP-B-51-33888, JP-B-56-52013, JP-B-59-50667, JP-B-60-36812, etc.

These catalysts, however, have the problem that when they are used for fluidized bed ammoxydation reaction of propylene, isobutene or tertiary butanol, the yield of acrylonitrile or methacrylonitrile decreases with time. Many factors are conceivable as causes of such decrease of yield and they are yet to be elucidated in more detail, but it is considered that the loss of molybdenum from the catalyst in the course of ammoxydation reaction is one of the causes. Various methods such as mentioned below have been proposed for preventing drop of catalyst performance by supplementing the loss of molybdenum: (1) the catalyst reduced in performance is once taken out of the reaction system and impregnated with a solution containing molybdenum; (2) a molybdenum compound supported on a carrier is added to the reaction system; (3) a molybdenum compound not supported on a carrier is added to the reaction system; (4) an oxide catalyst containing molybdenum and other necessary metal elements, of high molybdenum content, is added.

Regarding the method (1), specifically, JP-B-55-49541 (E.I. du Pont de Nemours & Co.) and JP-B-5-33100 (Enichem Sintesi Spa) disclose the idea that a molybdenum-containing multi-component oxide catalyst deactivated after use for the ammoxydation reaction be impregnated with a solution containing molybdenum or a solution containing molybdenum and bismuth and then calcined to form a regenerated catalyst, and this regenerated catalyst be used again for the ammoxydation reaction.

Relating to the method (2), JP-B-58-57422 (U.S. Pat. No. 3,882,159: The Standard Oil Company) mentions addition of silica-supported molybdenum oxide to the reactor during the fluidized bed ammoxydation reaction using a molybdenum-containing multi-component oxide catalyst. JP-A-59-193136 (Ube Industries, Ltd.) proposes to carry out ammoxydation reaction in a fixed bed in the presence of a molybdenum-containing oxide catalyst and molybdenum oxide supported on an inert carrier.

Concerning the method (3), DE-A-3,311,521 (SKW) discloses addition of a non-supported molybdenum compound, preferably molybdenum trioxide or ammonium molybdate, to the catalyst to be regenerated in a ratio of 0.25–2.5% by weight during the fluidized bed ammoxydation reaction using a molybdenum-containing oxide catalyst. Also, JP-B-2-56938 (Nitto Chemical Industries Co., Ltd.) proposes addition of non-supported solid molybdenum during the fluidized bed ammoxydation reaction using an oxide catalyst containing at least one element selected from the group consisting of vanadium, molybdenum and tungsten in addition to iron, antimony and tellurium.

According to the method (1), however, since the catalyst reduced in performance needs to be taken out of the reaction system and regenerated, the process is complicated, resulting in a substantial economical loss. So, means for recovering the catalyst performance in the course of the reaction have been sought, and this prompted proposal of the methods (2) and (3) in which a supported or non-supported molybdenum compound is added to the reaction system. These methods, however, still involve the problem that since the molybdenum compound to be added is different in physical properties from the catalyst in the reaction system, the molybdenum compound added in large quantities tends to adhere and accumulate on the cooling coils in the reactor or on the heat exchanger at the exit of the reactor, and such deposits need to be removed. Also, as mentioned in JP-B-2-56938, deactivation of the iron/antimony-based oxide catalyst is not considered to be caused by the loss of molybdenum, but it is considered that the recovery of catalyst activity by the addition of molybdenum is credited to the subsequent creation of new active sites on the catalyst. Therefore, the necessity of continuous addition of molybdenum in the catalyst system reflects the fact that the composition of the iron/antimony-based oxide catalyst changes with time, and thus it is considered that there is a limit to the long-time maintenance of catalyst performance. Further, in case a supported molybdenum compound is added to the reaction system, there arises the problem that the remaining carrier is accumulated in the reaction system.

Recently, with the background of these facts, there has been proposed the method (4) according to which the problems of the methods (1) to (3) are resolved by increasing the molybdenum content of the catalyst and also adding a compound whose elemental composition excluding molybdenum is analogous to that of the catalyst in the reaction system. For instance, U.S. Pat. No. 5,177,048 (China Petro-Chemical Corp.) and U.S. Pat. No. 5,378,668 (EC Erdolchemie GmbH) propose addition of an oxide catalyst containing molybdenum and other metal elements, of high molybdenum content, during the fluidized bed ammoxydation reaction using a molybdenum-containing multi-component oxide catalyst. It was found, however, that according to this method, since the catalyst contains metal elements other than molybdenum, there arise the problems such as difficulties in maintaining the composition of the catalyst in the reaction system and excess amounts of the additives, which makes it unable to realize stabilized long-time continuous production of acrylonitrile or methacrylonitrile.

An object of the present invention is to provide a process for producing acrylonitrile or methacrylonitrile by carrying out a fluidized bed ammoxydation reaction using a multi-component oxide catalyst containing molybdenum, which process is capable of preventing the yield from dropping with time and producing the objective product stably over a long time.

DISCLOSURE OF THE INVENTION

In the course of studies for overcoming the above problems, the present inventors found that when an ammoxydation reaction of propylene, isobutene or tertiary butanol is carried out by adding a non-supported molybdenum compound, which can be converted into molybdenum oxide, to the fluidized bed as its activator and maintaining the composition of the catalyst in the reaction system within a specified range, surprisingly, it is possible to realize a higher yield of acrylonitrile or methacrylonitrile by use of a catalyst having said activator added thereto than when using a catalyst with no said activator added with a same molybdenum content, and also such a high yield can be maintained constantly. The present invention has been achieved on the basis of the above finding.

The present invention is a process for producing acrylonitrile or methacrylonitrile which comprises carrying out a fluidized bed ammoxydation reaction of propylene, isobutene or tertiary butanol while adding an activator to the fluidized bed, wherein a molybdenum compound which is convertible to molybdenum oxide and not supported on a carrier is added as said activator to a fluidized bed reactor, and said fluidized bed ammoxydation reaction of propylene, isobutene or tertiary butanol is carried out in the presence of a catalyst comprising silica and an oxide catalyst represented by the formula:

$$Mo_yBi_pFe_qA_aB_bC_cD_dE_eO_f$$

(wherein Mo is molybdenum, Bi is bismuth, Fe is iron, A is at least one element selected from the group consisting of nickel and cobalt, B is at least one alkali metal element, C is at least one element selected from the group consisting of magnesium, calcium, strontium, barium, zinc, manganese, lead and cadmium, D is at least one rare earth element, E is at least one element selected from the group consisting of chromium, indium and gallium, O is oxygen; y is the ratio of molybdenum atoms during the ammoxydation reaction and y=1.02x–1.12x wherein x=1.5p+q+a+c+1.5d+1.5e; and p, q, a, b, c, d, e and f are the ratios of atoms of bismuth, iron, A, B, C, D, E and oxygen, respectively, but p=0.01–5, q=0.1–5, a=4–10, b=0.01–2, c=0–5, d=0–5, e=0–5, and f is the number of oxygen atoms necessary for satisfying the valence requirements of other elements present in the composition, the amount of silica being 30–70% by weight based on the total amount of said silica and said oxide catalyst, said oxide catalyst being supported on said silica, with the ratio y of molybdenum atoms in said oxide catalyst being maintained within the range of 1.02x to 1.12x.

The gist of the present invention resides in controlling the ratio of molybdenum atoms in the catalyst to stay within a specified range by adding an activator. According to the present invention, since the yield of acrylonitrile or methacrylonitrile can be maintained at a high level, it is possible to control deposition of scale on cooling coils in the reactor, heat exchanger at the exit of the reactor and the like, thus enabling stabilized long-time continuous operation of the reactor to realize constant yield of the objective product as well as the by-products, and this contributes to minimizing variation of the reactor operating conditions which will affect the working efficiency of the ensuing steps, and thereby facilitating the operations in the recovering and refining systems. Economical effect of the present invention is also notable since the inexpensive molybdenum compounds can be used as activator in the process of the present invention.

BEST MODE FOR CARRYING OUT THE INVENTION

The catalyst used in the present invention comprises silica and an oxide catalyst, wherein this oxide catalyst is supported on the above silica.

This oxide catalyst is represented by the formula:

$$Mo_yBi_pFe_qA_aB_bC_cD_dE_eO_f \qquad (I)$$

wherein Mo is molybdenum, Bi is bismuth, Fe is iron, A is at least one element selected from the group consisting of nickel and cobalt, B is at least one alkali metal element, C is at least one element selected from the group consisting of magnesium, calcium, strontium, barium, zinc, manganese, lead and cadmium, D is at least one rare earth element, E is at least one element selected from the group consisting of chromium, indium and gallium, O is oxygen; y is the ratio of molybdenum atoms during the ammoxidation reaction and y=1.02x–1.12x wherein x=1.5p+q+a+c+1.5d+1.5e; and p, q, a, b, c, d, e and f are the ratios of atoms of bismuth, iron, A, B, C, D, E and oxygen, respectively, but p=0.01–5, q=0.1–5, a=4–10, b=0.01–2, c=0–5, d=0–5, e=0–5, and f is the number of oxygen atoms necessary for satisfying the valence requirements of other elements present in the composition.

Preferably the above oxide catalyst is represented by the formula:

$$Mo_yBi_pFe_qA_aB_bC_cD_dO_f \qquad (II)$$

wherein Mo is molybdenum, Bi is bismuth, Fe is iron, A is at least one element selected from the group consisting of nickel and cobalt, B is at least one alkali metal element, C is at least one element selected from the group consisting of magnesium, calcium, strontium, barium, zinc, manganese, lead and cadmium, D is at least one rare earth element, O is oxygen; y is the ratio of molybdenum atoms during the ammoxidation reaction and y=1.02x–1.12x wherein x=1.5p+q+a+c+1.5d+1.5e; and p, q, a, b, c, d and f are the ratios of atoms of bismuth, iron, A, B, C, D and oxygen, respectively, but d/(p+d)=0.6–0.8, p+d=0.5–2, q=0.1–3, a=4–10, b=0.01–2, c=0–3, and f is the number of oxygen atoms necessary for satisfying the valence requirements of other elements present in the composition.

In the above formulae (I) and (II), A is preferably nickel, B is preferably at least one element selected from the group consisting of potassium, rubidium and cesium, C is preferably at least one element selected from the group consisting of magnesium and zinc, D is preferably at least one element selected from the group consisting of yttrium, lanthanum, cerium, praseodymium, neodymium and samarium, more preferably cerium.

In the present invention, the ratio (initial ratio) Y of molybdenum atoms in the oxide catalyst before use is not specified as to its range so far as the ratio (ratio during reaction) y of molybdenum atoms can maintain the above equation: y=1.02x–1.12x during the ammoxidation reaction. Preferably Y=0.9x–1.2x, more preferably Y=1.02x–1.12x.

A good catalyst performance can be obtained by selecting the composing elements of the oxide catalyst and the ratios of atoms of said element so as to satisfy the above conditions.

The oxide catalyst used in the present invention may further contain at least one element selected from the group consisting of phosphorus, antimony, tungsten, vanadium, tellurium and palladium in limited amounts.

Silica is used as the carrier of the oxide catalyst. Silica affords favorable physical properties such as fluidity and wear resistance to the above catalyst. It is suggested to add silica in an amount of 30–70% by weight, preferably 40–60% by weight, based on the total amount of said oxide catalyst and silica. If the amount of the carrier is less than 30% by weight, the catalyst will lack required mechanical strength, while use of the carrier in excess of 70% by weight leads to a reduced yield of acrylonitrile or methacrylonitrile.

According to the present invention, in the fluidized bed ammoxydation reaction, a molybdenum compound not supported on a carrier and convertible to molybdenum oxide is added as activator to said catalyst so that the ratio y of molybdenum atoms in the oxide catalyst will be maintained within the range, expressed with the above-defined x, of 1.02x to 1.12x, preferably 1.05x to 1.09x during the reaction. Thus, the above-mentioned effect can be obtained. When y is less than 1.02x, the yield of acrylonitrile or methacrylonitrile undesirably lowers, and when y exceeds 1.12x, combustion of ammonia becomes brisk, disadvantageously making it necessary to enlarge the molar ratio of ammonia to propylene in the feed gas for obtaining a satisfactory acrylonitrile or methacrylonitrile yield. Also, when y exceeds 1.12x, part of the activator added and the molybdenum released from the catalyst may be deposited on the internal structure of the reactor. Particularly in the industrial practice of the process, a large amount of molybdenum is deposited in the form of oxides on the external surface of the cooling coil placed inside the reactor to lower the heat transfer coefficient, hampering control of the reaction temperature and in some cases disenabling continuous operation of the process.

The molybdenum compounds usable as activator in the present invention include the molybdenum oxides represented by the formula $Mo_xO_y$ wherein a Y/X value is 1 to 3, such as $MoO_3$, $MoO_2$, $Mo_2O_3$, $Mo_3O_5$, $Mo_3O_8$, $Mo_4O_{11}$, $Mo_8O_{23}$ and $Mo_9O_{26}$; molybdic acids such as $H_2MoO_4$ and $H_2MoO_4 \cdot H_2O$; ammonium salts of molybdic acids such as $(NH_4)_2MoO_4$ and $(NH_4)_6Mo_7O_{24} \cdot 4H_2O$; molybdenum sulfides such as $MoS_3$ and $MoS_2$; molybdenum halides such as $MoOCl_4$, $MoO_2Cl_3$, $MoOCl_3$, $MoCl_5$ and $MoCl_4$; carbonyl compounds of molybdenum such as $Mo(CO)_6$, $(C_5H_5)Mo(CO)_5Mo(C_5H_5)$, $(C_5H_5)Mo(CO)_3H$, $Mo(CO)_3(C_5H_5N)_3$ and $Mo_2(CO)_6(H_2NCH_2CH_2NH_2)_3$; and cyano compounds of molybdenum such as $H_4[Mo(CN)_7(OH)_2]$. Of these molybdenum compounds, molybdenum trioxide ($MoO_3$), molybdic acids ($H_2MOO_4$ and $H_2MoO_4 \cdot H_2O$), ammonium molybdate (($NH_4)_2MoO_4$) and ammonium paramolybdate (($NH_4)_6Mo_7O_{24} \cdot 4H_2O$] are preferred. Ammonium paramolybdate (($NH_4)_6Mo_7O_{24} \cdot 4H_2O$) is more preferred. These molybdenum compounds may be used either singly or as a mixture of two or more of them.

The molybdenum compound is used without being supported on a carrier. When the molybdenum compound is supported on silica, although a temporary catalyst activating effect is produced, it is hardly possible to maintain the reaction performance at a high level constantly for a prolonged period of time, so that it is undesirable to support the molybdenum compound on a carrier.

In the present invention, the particle size of the molybdenum compound used as activator is not specified, but it is preferably within a range from 1 μm to 4 mm. Supply of the molybdenum compound to the reactor can be effected by forcedly passing the molybdenum compound through a pipe into the reactor with a gaseous body such as air or nitrogen. The molybdenum compound is preferably supplied to the dense phase in the fluidized bed reactor, particularly to the bottom portion of such the dense phase so that the molybdenum compound will be allowed to contact sufficiently with the catalyst.

The catalyst in the reactor decreases with time due to various factors such as attrition and insufficient particle collecting efficiency of the cyclone, so that it needs to be supplemented during the reaction operation. In some cases, it is desirable to add the molybdenum compound mixed with the catalyst to be supplemented.

The amount of the activator to be added for maintaining the ratio y of molybdenum atoms within the above-defined range in the present invention is an amount corresponding to 0.006x or less, preferably 0.004x or less, per one addition. Such an amount of activator is added at a frequency of once or more every one to 30 days, preferably once or more every ½ to 15 days, more preferably once or more every ⅓ to 7 days. It is preferred to add the activator at a high frequency in an amount corresponding to 0.004x or less per one addition. It is also recommendable to add the activator continuously.

In case the amount of the activator added exceeds the amount corresponding to 0.006x per one addition, especially when it is an amount corresponding to 0.01x or more, enhancement of the yield of acrylonitrile or methacrylonitrile is diminished due to reduction of conversion of propylene, isobutene or tertiary butanol and increased combustion of ammonia. Also, part of the activator (molybdenum) added is deposited on the internal structure of the reactor, making it difficult to carry on the reaction stably for a long time.

The catalyst composition can be analyzed by various methods such as fluorescent X-ray analysis, atomic-absorption spectroscopy, inductivity coupled plasma-optical emission analytical spectrometry (ICP), etc.

Since the ratio of molybdenum atoms in the catalyst in the reactor is subject to change depending on the operating conditions and other factors, the amount of the activator added and the frequency of addition can be properly changed by monitoring the ratio of molybdenum atoms in the catalyst in the reactor so that the ratio will be kept within the range specified in the present invention.

The catalyst used in the present invention can be prepared by known methods. For instance, it can be produced by spray drying a mixed solution of catalyst materials and calcining the dried product. In preparing catalyst materials, it is recommended to use water-soluble compounds, for example, silica sol as silica material, ammonium salt, etc. as molybdenum material and nitrates, etc. as other component materials. In the spray drying of the mixed solution of catalyst materials, a centrifugal spray system is preferably employed. The drying temperature is 100–400° C., preferably 150–300° C. Calcination of the dried product is conducted in a temperature range of 500–750° C., preferably 550–700° C., for 1–20 hours, if necessary after preliminary calcination at 150–500° C.

The starting materials such as propylene, isobutene or tertiary butanol, ammonia, etc., used for the ammoxydation reaction in the present invention need not be high-purity preparations but may be of commercial grade. Air is preferably used as oxygen source, but it is also possible to use a gas of an increased oxygen concentration such as formed by mixing oxygen with air.

In the ammoxydation reaction, the molar ratio of propylene, isobutene or tertiary butanol, ammonia and air in the feed gas composition is 1:0.9–1.3:8–10. The reaction temperature is 400–470° C., preferably 420–450° C., and the reaction pressure is in a range from normal pressure to 3 atm. The contact time between the feed gas and the catalyst is 0.5–20 sec.g/ml, preferably 1–10 sec.g/ml.

The present invention will be further illustrated by the following examples and comparative examples, but these examples are not to be construed as limiting the scope of the invention.

In the following Examples and Comparative Examples, the reaction was carried out using a 3-inch SUS 304 fluidized bed reactor under a pressure P of 0.5 kg/cm$^2$G.

The contact time is defined as follows:

Contact time (sec.g/ml)=$(W/F) \times 273/(273+T) \times (1.03+P)/1.03$ wherein
W: amount of catalyst (g);
F: amount of gas supplied (ml/sec; reduced to NPT basis);
T: reaction temperature (°C.);
P: reaction pressure (kg/cm$^2$G).

The conversion and yield shown here as the indices of the reaction result are defined as follows:

Conversion (%)=(number of moles of propylene reacted)/(number of moles of propylene supplied)×100

Yield (%)=(number of moles of acrylonitrile produced)/(number of moles of propylene supplied)×100

EXAMPLE 1

Present Invention

A catalyst comprising an oxide of the composition $Mo_{12.0}Bi_{0.20}Ce_{0.40}Fe_{2.0}Ni_{5.6}Mg_{2.2}K_{0.07}Cs_{0.04}$ supported on 50% by weight of silica was prepared in the manner described below. In this catalyst, x was 10.7, and the ratio of molybdenum atoms y was 1.12x.

To 3,333.4 g of silica sol containing 30% by weight of $SiO_2$ was added a solution prepared by dissolving 38.6 g of bismuth nitrate [$Bi(NO_3)_3 \cdot 5H_2O$], 69.0 g of cerium nitrate [$Ce(NO_3)_3 \cdot 6H_2O$], 321.2 g of iron nitrate [$Fe(NO_3)_3 \cdot 9H_2O$, 647.6 g of nickel nitrate [$Ni(NO_3)_2 \cdot 6H_2O$], 224.2 g of magnesium nitrate [$Mg(NO_3)_2 \cdot 6H_2O$], 2.82 g of potassium nitrate [$KNO_3$] and 3.10 g of cesium nitrate [$CsNO_3$] in 755.4 g of 17.9% by weight nitric acid, and finally a solution of 842.4 g of ammonium paramolybdate [$(NH_4)_6Mo_7O_{24} \cdot 4H_2O$] in 1,696.6 g of water was added. The resultant mixed solution was supplied to a parallel flow type spray dryer and dried at about 200° C. Spraying of the solution was effected by a sprayer having a dish type rotor set centrally in the upper part of the dryer. The obtained powder was subjected to preliminary calcination at 400° C. for 1 hour in an electric furnace and then calcined at 590° C. for 2 hours to prepare a catalyst.

Using 1,400 g of this catalyst, an ammoxydation reaction of propylene was carried out by supplying a mixed gas of reactants having a propylene/ammonia/air molar ratio of 1/1.10/9.0, setting the reaction temperature at 430° C. and the contact time at 6.0 sec.g/ml as ordinary reaction conditions. The conversion after approximately 100 hours from start of the reaction was 99.8% and the yield of acrylonitrile was 80.8%. About 5 g of the catalyst was sampled out from the reactor and its composition was analyzed by a fluorescent X-ray analyzer, which showed the ratio of molybdenum atom was 12.0 (y=1.12x).

Then, to make the reaction conditions more harsh, the reaction temperature was raised to 460° C., the prolylene/ammonia/ air molar ratio of the reactant gas supplied was adjusted so that the ammonia concentration and the oxygen concentration at the exit of the reactor would become 0.1–1.0% by volume and 0.05–0.5% by volume, respectively, and the contact time was 3.7 sec.g/ml. The process was run under these harsh reaction conditions for one month and then returned to the original normal reaction conditions. Analysis of the reaction gas showed 99.3% conversion and 80.0% yield of acrylonitrile. The ratio of molybdenum atom in the catalyst sampled out from the reactor was 11.7 (y=1.09x).

The process was again carried out under the harsh reaction conditions mentioned above for two weeks and then returned to the original normal reaction conditions. The conversion was 99.1% and the yield of acrylonitrile was 79.5%. The ratio of molybdenum atoms in the catalyst sampled out from the reactor was 11.6 (y=10.8x).

The process was further operated under the harsh reaction conditions for two more weeks and then returned to the original normal conditions. The conversion in this operation was 98.9% and the yield of acrylonitrile was 78.9%. The ratio of molybdenum atoms in the catalyst sampled out from the reactor was 11.5 (y=1.07x).

Then, under the normal reaction conditions, 2.0 g of ammonium paramolybdate [$(NH_4)_6Mo_7O_{24} \cdot 4H_2O$] corresponding to 0.004x=0.043 was added to the reactor three times at an interval of two days. The conversion in this operation was 99.0% and the yield of acrylonitrile was 80.4%. The ratio of molybdenum atoms in the catalyst sampled out from the reactor was 11.6 (y=1.08x).

The operation was further continued under the normal reaction conditions by adding 0.5 g of ammonium paramolybdate [$(NH_4)_6Mo_7O_{24} \cdot 4H_2O$] with 0.001x=0.011 to the reactor three times at an interval of one week. This operation provided 99% conversion and 80–81% yield of acrylonitrile. The valence of molybdenum in the catalyst sampled out from the reactor after final addition of ammonium paramolybdate was 11.6 (y=1.08x).

Through this series of reactions, the catalyst composition remained substantially unchanged in ratios of atoms of other components than molybdenum. Also, no white particle was observed in the sampled out catalyst.

These results show that by the addition of an activator to the reaction system, it is possible to enhance the yield of acrylonitrile without increasing the molar ratio of ammonia to propylene in the feed gas. Also, there can be obtained a higher acrylonitrile yield than when no activator is added with a same ratio of molybdenum atoms, and this high acrylonitrile yield can be maintained constantly. Further, from the fact that no white particle was admitted in the sampled-out catalyst, it is seen that the added activator acts effectively to the catalyst and is scarcely deposited on the internal structure of the reactor, etc.

EXAMPLE 2

Present Invention

The catalyst was prepared in the same manner as in Example 1 except that the composition of the oxide as $Mo_{11.8}Bi_{0.45}Ce_{0.90}Fe_{1.8}Ni_{5.0}Mg_{2.0}K_{0.09}Rb_{0.05}$, and that calcination was carried out at 610° C. for 2 hours. In this catalyst, x was 10.8 and the ratio of molybdenum atoms y was 1.09x.

Using this catalyst, an ammoxydation reaction of propylene was carried out under the normal reaction conditions same as in Example 1 except that the contact time was 6.7 sec.g/ml. The conversion after about 100 hours from start of the reaction was 99.6%, and the yield of acrylonitrile was 81.8%. The ratio of molybdenum atoms in the catalyst sampled out from the reactor was 11.8 (y=1.09x).

Then the process was further run under the harsh reaction conditions same as in Example 1 for two weeks and then returned to the original normal reaction conditions. The reaction gas analysis showed 99.3% conversion and 81.1% yield of acrylonitrile. The ratio of molybdenum atoms in the catalyst sampled out from the reactor was 11.7 (y=1.08x).

Then the process was again operated under the harsh reaction conditions for two weeks and then returned to the original reaction conditions. This operation provided 99.0% conversion and 80.6% yield of acrylonitrile. The ratio of molybdenum atoms in the catalyst sampled out from the reactor was 11.6 (y=1.07x).

Then, under the normal reaction conditions, 3.0 g of ammonium paramolybdate [$(NH_4)_6Mo_7O_{24} \cdot 4H_2O$] corresponding to 0.006x=0.065 was mixed with 7.5 g of the catalyst prepared in this Example, and the mixture was supplied to the reactor twice at an interval of three days. There were provided 99.1% conversion and 81.8% yield of acrylonitrile. The ratio of molybdenum atoms in the catalyst sampled out from the reactor was 11.7 (y=1.08x).

The operation was further continued under the normal reaction conditions by supplying 0.5 g of ammonium paramolybdate $[(NH_4)_6Mo_7O_{24}.4H_2O]$ corresponding to 0.001x=0.011 to the reactor three times at an interval of one week. This provided approximately 99% conversion and approximately 82% yield of acrylonitrile. The ratio of molybdenum atoms in the catalyst sampled out from the reactor after final addition of ammonium paramolybdate was 11.7 (y=1.08x).

In this series of reactions, the catalyst composition remained substantially unchanged in ratios of atoms of other components than molybdenum.

From these results, it is seen that the addition of an activator to the reaction system makes it possible to enhance the yield of acrylonitrile without increasing the molar ratio of ammonia to propylene in the feed gas, and that a higher yield of acrylonitrile can be obtained than when no activator is added with a same ratio of molybdenum atoms, and this high yield of acrylonitrile can be maintained steadily. Also, since no white particle was admitted in the sampled-out catalyst, it is seen that the added activator acts effectively to the catalyst and is scarcely deposited on the internal structure of the reactor, etc.

EXAMPLE 3

Present Invention

The catalyst was prepared in the same manner as in Example 1 except that the composition of the oxide was changed to $Mo_{11.4}Bi_{0.60}dCe_{1.20}Fe_{1.6}Ni_{4.8}Mg_{1.9}K_{0.11}Rb_{0.05}$, and that calcination was carried out at 600° C. for 2 hours. In this catalyst, x was 11.0 and the ratio of molybdenum atoms y was 1.04x.

Using this catalyst, an ammoxydation reaction of propylene was carried out under the normal reaction conditions same as in Example 1 except the contact time was changed to 6.2 sec.g/ml. The conversion after about 100 hours from start of the reaction was 99.5% and the yield of acrylonitrile was 79.4%. The ratio of molybdenum atoms in the catalyst sampled out from the reactor was 11.4 (y=1.04x).

Then the process was carried out under the harsh reaction conditions same as in Example 1 for two weeks and then returned to the original normal reaction conditions. Reaction gas analysis showed 99.2% conversion and 78.6% yield of acrylonitrile. The ratio of molybdenum atoms in the catalyst sampled out from the reactor was 11.3 (y=1.03x).

The process was again operated under the harsh reaction conditions for two weeks and then returned to the original normal reaction conditions. This operation provided 98.8% conversion and 77.4% yield of acrylonitrile. The ratio of molybdenum atoms in the catalyst sampled out from the reactor was 11.2 (y=1.02x).

Then, under the normal reaction conditions, 3.0 g of ammonium paramolybdate $[(NH_4)_6Mo_7O_{24}.4H_2O]$ corresponding to 0.006x=0.066 was supplied to the reactor twice at an interval of one day. Conversion was 99.0% and acrylonitrile yield was 79.3%. The ratio of molybdenum atoms in the catalyst sampled out from the reactor was 11.3 (y=1.03x).

The operation was further continued under the normal reaction conditions by supplying 0.5 g of ammonium paramolybdate $[(NH_4)_6Mo_7O_{24}.4H_2O]$ corresponding to 0.001x=0.011 to the reactor three times at an interval of one week. Conversion was about 99% and acrylonitrile yield was about 79%. The ratio of molybdenum atoms in the catalyst sampled out from the reactor after final addition of ammonium paramolybdate was 11.3 (y=1.03x).

In this series of reactions, the catalyst composition remained substantially unchanged in ratios of atoms of other components than molybdenum.

From these results, it is seen that the addition of an activator makes it possible to enhance the yield of acrylonitrile without increasing the molar ratio of ammonia to propylene in the feed gas, and that there can be obtained a higher acrylonitrile yield that when no activator is added with a same ratio of molybdenum atoms, and such a high acrylonitrile yield can be maintained constantly. Also, since no white particle was admitted in the sampled-out catalyst, it is seen that the added activator acts effectively to the catalyst and is scarcely deposited on the internal structure of the reactor, etc.

EXAMPLE 4

Comparison

Using the catalyst prepared in Example 3, the same operation as in Example 3 was carried out except that no ammonium paramolybdate $[(NH_4)_6Mo_7O_{24}.4H_2O]$ was added. The conversion after about 100 hours from start of the reaction was 99.4% and the yield of acrylonitrile was 79.5%. The ratio of molybdenum atoms in the catalyst sampled out from the reactor was 11.4 (y=1.04x).

Then the process was carried out under the harsh reaction conditions for two weeks and then returned to the original normal reaction conditions. Reaction gas analysis showed 99.2% conversion and 78.6% yield of acrylonitrile. The ratio of molybdenum atoms in the catalyst sampled out from the reactor was 11.3 (y=1.03x).

The process was again operated under the harsh reaction conditions for two weeks and then returned to the original normal reaction conditions. Conversion was 98.9% and acrylonitrile yield was 77.4%. The ratio of molybdenum atoms in the catalyst sampled out from the reactor was 11.2 (y=1.02x).

The process was further operated under the harsh reaction conditions for two weeks and then returned to the original normal reaction conditions. In this operation, the conversion was 98.6% and the yield of acrylonitriled dropped to 76.0%. The ratio of molybdenum atoms in the catalyst sampled out from the reactor was 11.1 which correspond to y=1.01x.

The above results show that when the operation is continued without adding the activator, the ratio of molybdenum atoms y in the catalyst lowers, and when it becomes smaller than the lower limit of the defined range in the present invention, the yield of acrylonitrile drops sharply.

EXAMPLE 5

Comparison

Using the catalyst prepared in Example 1, the same operation as in Example 1 was carried out except that the harsh reaction conditions were not applied.

The conversion after about 100 hours from start of the reaction was 99.7% and the yield of acrylonitrile was 80.9%. The ratio of molybdenum atoms in the catalyst sampled out from the reactor was 12.0 (y=1.12x).

Then, under the normal reaction conditions, 3.0 g of ammonium paramolybdate $[(NH_4)_6Mo_7O_{24}.4H_2O]$ corresponding to 0.006x=0.064 was supplied to the reactor six times at an interval of one day. The conversion lowered to 99.5% while the yield of acrylonitrile dropped to 78.9%. When the molar ratio of ammonia to propylene was raised from 1.10 to 1.15, the conversion was 99.3% and the yield of acrylonitrile was 80.6%. The ratio of molybdenum atoms in the catalyst sampled out from the reactor was 12.2 which corresponded to y=1.14x.

In this series of reactions, the catalyst composition remained substantially unchanged in ratios of atoms of other components than molybdenum.

From the overhaul of the reactor conducted after completion of the reaction detected, white deposits composed of molybdenum oxide were found on the inter walls of the reactor, etc. There were also found white particles, probably composed of molybdenum oxide, in the sampled-out catalyst.

These results show that when an activator is added to such an extent that the ratio of molybdenum atoms y in the catalyst will exceed the upper limit of the range defined in the present invention, the yield of acrylonitrile lowers, so that it is necessary for increasing the yield of acrylonitrile to raise the molar ratio of ammonia to propylene in the feed gas, which is economically disadvantageous. Also, since the white particles are admitted in the sampled-out catalyst, it is seen that the added activator does not act properly to the catalyst and tends to be deposited on the internal structure of the reactor to cause troubles such as the lowering of the heat transfer coefficient.

INDUSTRIAL APPLICABILITY

According to the process of the present invention, it is possible to maintain the yield of acrylonitrile or methacrylonitrile at a high level by adding a molybdenum compound not supported on a carrier to the reaction system to hold the catalyst composition of the reaction system in a specified range. Also, the process of the present invention not only enables stabilized long-time continuous prosecution of the reaction but also facilitates the operations of the recovering and refining systems. The process is also economically advantageous as it permits use of inexpensive molybdenum compounds.

This application claims a priority based on Japanese Patent Application No. 08-054,473 filed on Mar. 12, 1996, the content of which is herein incorporated by reference in its entirety.

We claim:

1. A process for producing acrylonitrile or methacrylonitrile which comprises carrying out a fluidized bed ammoxydation reaction of propylene, isobutene or tertiary butanol while adding an activator to the fluidized bed, wherein a molybdenum compound which is convertible to molybdenum oxide and not supported on a carrier is added as said activator to a fluidized bed reactor, and said fluidized bed ammoxydation reaction of propylene, isobutene or tertiary butanol is carried out in the presence of a catalyst comprising silica and an oxide catalyst represented by the formula:

$$Mo_yBi_pFe_qA_aB_bC_cD_dE_eO_f$$

(wherein Mo is molybdenum, Bi is bismuth, Fe is iron, A is at least one element selected from the group consisting of nickel and cobalt, B is at least one alkali metal element, C is at least one element selected from the group consisting of magnesium, calcium, strontium, barium, zinc, manganese, lead and cadminum, D is at least one rare earth element, E is at least one element selected from the group consisting of chromium, indium and gallium, O is oxygen; y is a ratio of molybdenum atoms during the ammoxidation reaction and y=1.02x–1.12x wherein x=1.5p+q+a+c+1.5d+1.5e; and p, q, a, b, c, d, e and f are ratios of atoms of bismuth, iron, A, B, C, D, E and oxygen, respectively, but p=0.01–5, q=0.1–5, a=4–10, b=0.01–2, c=0–5, d=0–5, e=0–5, and f is the number of oxygen atoms necessary for satisfying the valence requirements of other elements present in the composition), the amount of silica being 30–70% by weight based on the total amount of said silica and said oxide catalyst, said oxide catalyst being supported on said silica, with the ratio of molybdenum atoms y in said oxide catalyst being maintained in the range of 1.02x to 1.12x.

2. The process according to claim 1 wherein the activator is added at a frequency of once or more every one to 30 days.

3. The process according to claim 2 wherein the ratio of molybdenum atoms y is maintained in the range of 1.05x to 1.09x.

4. The process according to claim 3 wherein the activator is at least one molybdenum compound selected from the group consisting of molybdenum trioxide, molybdic acid, ammonium molybdate and ammonium paramolybdate.

5. The process according to any one of claims 1–4 wherein the activator is added in an amount corresponding to 0.006x or less per one addition.

6. The process according to any one of claims 1–4 wherein the activator is added in an amount corresponding to 0.004x or less per one addition.

* * * * *